(12) United States Patent
Carbunaru et al.

(10) Patent No.: US 7,953,498 B1
(45) Date of Patent: May 31, 2011

(54) RESORBABLE ANCHOR ARRANGEMENTS FOR IMPLANTABLE DEVICES AND METHODS OF MAKING AND USING

(75) Inventors: Rafael Carbunaru, Studio City, CA (US); Todd K. Whitehurst, Santa Clarita, CA (US); Kirsten N. Jaax, Saugus, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 72 days.

(21) Appl. No.: 11/376,360

(22) Filed: Mar. 15, 2006

(51) Int. Cl.
*A61N 1/375* (2006.01)
(52) U.S. Cl. .......................................................... 607/118
(58) Field of Classification Search .......... 607/126–132, 607/16–18, 118, 148–152
See application file for complete search history.

(56) References Cited

U.S. PATENT DOCUMENTS

| | | | |
|---|---|---|---|
| 3,941,136 A | 3/1976 | Bucalo | |
| 4,033,357 A | 7/1977 | Helland et al. | |
| 4,135,518 A | 1/1979 | Dutcher | |
| 4,301,815 A | 11/1981 | Doring | |
| 4,475,560 A * | 10/1984 | Tarjan et al. | 607/128 |
| 4,542,753 A | 9/1985 | Brenman et al. | |
| 4,585,005 A | 4/1986 | Lue et al. | |
| 4,628,944 A * | 12/1986 | MacGregor et al. | 607/126 |
| 4,702,254 A | 10/1987 | Zabara | |
| 4,722,353 A | 2/1988 | Sluetz | |
| 4,796,643 A | 1/1989 | Nakazawa et al. | |
| 4,867,164 A | 9/1989 | Zabara | |
| 4,957,118 A | 9/1990 | Erlebacher | |
| 5,025,807 A | 6/1991 | Zabara | |
| 5,193,539 A | 3/1993 | Schulman et al. | |
| 5,193,540 A | 3/1993 | Schulman et al. | |
| 5,312,439 A | 5/1994 | Loeb | |
| 5,314,457 A | 5/1994 | Jeutter et al. | |
| 5,376,108 A | 12/1994 | Collins et al. | |
| 5,433,735 A | 7/1995 | Zanakis et al. | |
| 5,439,938 A | 8/1995 | Snyder et al. | |
| 5,454,840 A | 10/1995 | Krakovsky et al. | |
| 5,480,420 A * | 1/1996 | Hoegnelid et al. | 607/116 |
| 5,571,118 A | 11/1996 | Boutos | |
| 5,741,319 A * | 4/1998 | Woloszko et al. | 607/118 |
| 5,775,331 A | 7/1998 | Raymond et al. | |
| 5,922,015 A * | 7/1999 | Schaldach | 607/126 |
| 5,931,864 A * | 8/1999 | Chastain et al. | 607/128 |

(Continued)

FOREIGN PATENT DOCUMENTS

WO    WO 98/37926    9/1998

(Continued)

OTHER PUBLICATIONS

"Tissue" Definition, Stedman's Medical Dictionary, 27th Edition, Copyright 2000. Printed Aug. 10, 2009 from http://www.thomsonhc.com.*

(Continued)

*Primary Examiner* — Scott M Getzow
*Assistant Examiner* — Amanda Patton
(74) *Attorney, Agent, or Firm* — Frommer Lawrence & Haug LLP; Patrick R. Turner

(57) ABSTRACT

An implantable device includes a device body and at least one anchoring unit configured and arranged for anchoring the device body in a patient upon implantation. The anchoring unit includes a resorbable material that resorbs into the patient over a period of time after implantation.

14 Claims, 2 Drawing Sheets

U.S. PATENT DOCUMENTS

| | | | |
|---|---|---|---|
| 5,938,584 A | 8/1999 | Ardito et al. | |
| 6,051,017 A | 4/2000 | Loeb et al. | |
| 6,058,332 A | 5/2000 | Dahl | |
| 6,181,969 B1 | 1/2001 | Gord | |
| 6,188,932 B1 | 2/2001 | Lindegren | |
| 6,463,335 B1 * | 10/2002 | Munch et al. | 607/129 |
| 6,516,227 B1 | 2/2003 | Meadows et al. | |
| 6,600,956 B2 * | 7/2003 | Maschino et al. | 607/118 |
| 6,609,029 B1 | 8/2003 | Mann et al. | |
| 6,609,032 B1 | 8/2003 | Woods et al. | |
| 6,650,943 B1 | 11/2003 | Whitehurst et al. | |
| 6,735,474 B1 | 5/2004 | Loeb et al. | |
| 6,741,892 B1 | 5/2004 | Meadows et al. | |
| 6,788,975 B1 | 9/2004 | Whitehurst et al. | |
| 7,054,692 B1 * | 5/2006 | Whitehurst et al. | 607/149 |
| 2003/0236558 A1 * | 12/2003 | Whitehurst et al. | 607/45 |
| 2004/0059392 A1 | 3/2004 | Parramon et al. | |
| 2005/0119718 A1 * | 6/2005 | Coe et al. | 607/130 |
| 2006/0241737 A1 * | 10/2006 | Tockman et al. | 607/126 |

FOREIGN PATENT DOCUMENTS

| | | |
|---|---|---|
| WO | WO 98/43700 | 10/1998 |
| WO | WO 98/43701 | 10/1998 |

OTHER PUBLICATIONS

U.S. Appl. No. 11/040,209, filed Jan. 20, 2005 by Colvin et al., for "Implantable Microstimulator with Plastic Housing and Methods of Manufacture and Use".

U.S. Appl. No. 11/056,762, filed Feb. 11, 2005 by Tom He, for "An Impantable Microstimulator Having a Separate Battery Unit and Methods of Use Thereof".

U.S. Appl. No. 11/238,240, filed Sep. 29, 2005 by He et al., for "Implantable stimulator with Integrated Plastic Housing/Metal Contacts and Manufacture and Use".

U.S. Appl. No. 11/294,283, filed Dec. 5, 2005 by Whitehurst et al., for "Cuff Electrode Arrangement for Nerve Stimulation and Methods of Treating Disorders".

U.S. Appl. No. 11/311,502, filed Dec. 19, 2005 by Whitehurst et al., for "Electrode Arrangement for Nerve Stimulation and Methods of Treating Disorders".

U.S. Appl. No. 11/393,991, filed Mar. 30, 2006 by Moffitt et al., for "Electrode Contact Configurations for Cuff Leads".

Rattay, F., "Analysis of Models for External Stimulation of Axons," IEEE Transactions on Biomedical Engineering, BME-33(10):974-977, 1986.

* cited by examiner

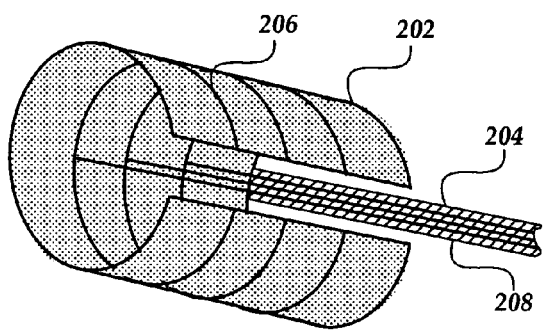
Fig. 4
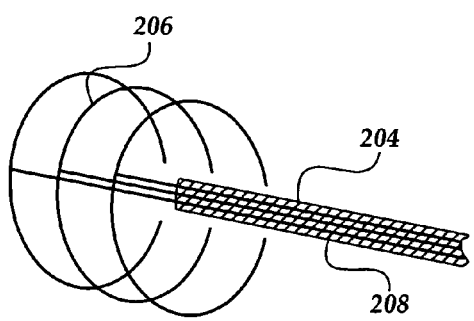
Fig. 5
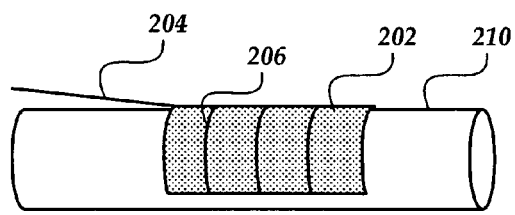
Fig. 6
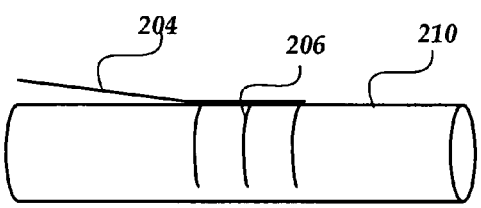
Fig. 7
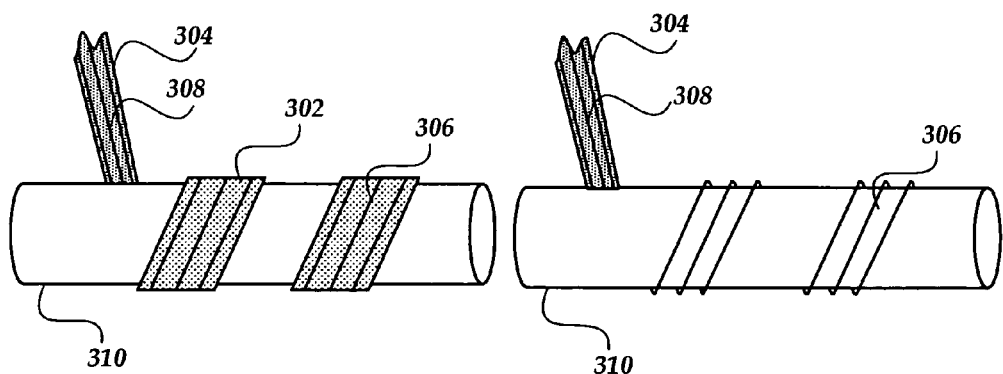
Fig. 8
Fig. 9

US 7,953,498 B1

RESORBABLE ANCHOR ARRANGEMENTS FOR IMPLANTABLE DEVICES AND METHODS OF MAKING AND USING

FIELD

The invention is directed to implantable devices that include resorbable anchor arrangements, and methods of making and using the devices. In addition, the invention is directed to implantable leads having one or more resorbable anchor arrangements and methods of making and using the leads.

BACKGROUND

Implantable electrical stimulation devices have proven therapeutic in a variety of diseases and disorders. For example, pacemakers and implantable cardiac defibrillators have proven effective in the treatment of cardiac conditions. Spinal cord stimulation systems have been used as a therapeutic modality for the treatment of chronic pain syndromes. Deep brain stimulation has also been useful for treating refractory chronic pain syndromes and has been applied to treat movement disorders and epilepsy. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Implantable drug delivery systems allow highly concentrated drugs to be delivered to specific sites. This site specific delivery can result in reduced side effects, improved quality of life, and, in some cases, may extend life. Such drug delivery systems include both programmable pumps and constant flow pumps. Examples of such systems include intrathecal drug delivery for the treatment of chronic intractable pain; delivery of baclofen for the treatment of spasticity; site specific delivery of drugs for the treatment of cancer, and site specific insulin delivery for the management of diabetes.

One disadvantage of these devices is that the electrode lead or drug catheter may migrate within the body. Migration may result in failure of the therapy or unwanted side effects. A variety of methods have been used to fix the lead or catheter including sutures and cuffs. While such fixation can be useful to prevent or reduce lead or catheter migration, many leads and catheters are eventually removed due to, for example, patient request, therapy completion or failure, infection, etc. These fixation methods can make removal of the implantable device more difficult.

BRIEF SUMMARY

One embodiment is an implantable device that includes a device body and at least one anchoring unit configured and arranged for anchoring the device body in a patient upon implantation. The anchoring unit includes a resorbable material that resorbs into the patient over a period of time after implantation.

Another embodiment is a method of implanting a device. The method includes implanting an implantable device body and coupling an anchoring unit to tissue. The anchoring unit allows fixation of the device body to the tissue. The anchoring unit includes resorbable material.

Yet another embodiment is an implantable device that includes a control unit, an implantable device body combined with the control unit and configured and arranged to be implanted proximate to selected tissue in a patient, and at least one anchoring unit configured and arranged for anchoring the implantable device body in the patient upon implantation. The anchoring unit includes a resorbable material that resorbs into the patient over a period of time after implantation.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 4 is a schematic perspective view of a fourth embodiment of an implantable device with a resorbable anchor arrangement, according to the invention;

FIG. 5 is a schematic perspective view of the implantable device of FIG. 4 disposed over a nerve;

FIG. 6 is a schematic perspective view of the implantable device of FIG. 4 with the resorbable anchor arrangement removed;

FIG. 7 is a schematic perspective view of the implantable device of FIG. 4 disposed over a nerve and with the resorbable anchor arrangement removed;

FIG. 8 is a schematic perspective view of a fifth embodiment of an implantable device with a resorbable anchor arrangement wrapped helically around a nerve, according to the invention; and FIG. 9 is a schematic perspective view of the implantable device of FIG. 8 with the resorbable anchor arrangement removed.

DETAILED DESCRIPTION

Figure 1:
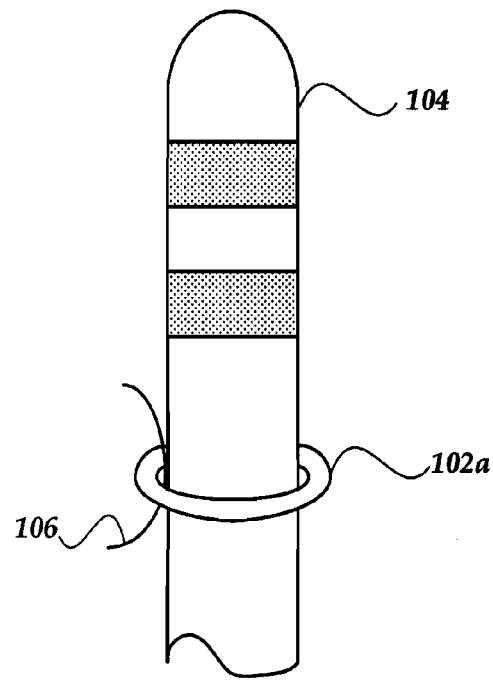
FIG. 1 is a schematic perspective view of one embodiment of an implantable device with a resorbable anchor arrangement, according to the invention.

The invention is directed to implantable devices that include resorbable anchor arrangements, and methods of making and using the devices. In addition, the invention is directed to implantable leads having one or more resorbable anchor arrangements and methods of making and using the leads.

Suitable implantable devices include, but are not limited to, electrode leads, catheters, sensors, and transmitters. For example, the implantable device can be an electrode lead with one or more electrodes disposed on a distal end of the lead and one or more terminals disposed on a proximal end of the lead. One embodiment of a resorbable anchor arrangement includes the electrodes disposed on the resorbable material. In another embodiment, the resorbable anchor arrangement can be disposed around or attached to the electrode lead. Electrodes leads include, for example, percutaneous leads and paddle leads. Examples of stimulator systems with electrode leads are found in U.S. Pat. Nos. 6,181,969; 6,516,227;

6,609,029; 6,609,032; and 6,741,892; and U.S. patent application Ser. No. 11/238,240, all of which are incorporated by reference.

A resorbable anchor arrangement can also be used to fix a microstimulator in place. Examples of suitable microstimulators are described in U.S. Pat. Nos. 5,193,539; 5,193,540; 5,312,439; 6,051,017; and 6,609,032; U.S. Patent Application Publication No. 2004/059392; U.S. patent applications Ser. Nos. 11/040,209 and 11/056,762; and PCT Patent Applications Publication Nos. 98/37926; 98/43700; and 98/43701, all of which are incorporated herein by reference. The BION™ microstimulator, available from Advanced Bionics Corporation, Sylmar, Calif., is an example of a microstimulator.

A resorbable anchor arrangement can also be used to fix a catheter in place. For example, the catheter can be a portion of an implantable drug delivery system. The catheter is typically implanted in the proximity of the tissue to be treated.

Implantable sensors can also be fixed using a resorbable anchor arrangement. Examples of sensors include, but are not limited to, electrical activity sensors (e.g., electroencephalograph, electrocardiograph, electromyograph, and electronystagmograph sensors); chemical sensors (e.g., glucose and drug sensors); and mechanical activity sensors (e.g., pressure, strain, stress, position, velocity, and acceleration sensors.)

These types of implantable devices can also be combined. For example, an electrode lead may also include a catheter lumen to provide drugs or other medications to the tissue to be stimulated or to other proximate tissue. As another example, an electrode lead can include one or more of the sensors described above. Yet another example is a catheter that includes one or more of the above-described sensors.

The resorbable anchor arrangement allows the implantable device to be fixed to the tissue at the implantation site using, for example, sutures, staples, and adhesive, or by at least partially wrapping the resorbable anchor arrangement around the tissue, for example, as a cuff or as a ribbon wrapped around a portion of a nerve, vein, artery, muscle, ligament, or organ. The resorbable material of the anchor arrangement is resorbed by the body of the patient over time. The resorbtion typically releases, at least partially, the implantable device from the anchor arrangement. This release can assist in the later removal of the implantable device. In some instances, the implantable device may even be withdrawn from the implantation site by pulling on the device (e.g., on an electrode lead or catheter.)

The resorbtion time for the resorbable material can be selected, if desired, to provide an average lifetime for the anchoring arrangement. For example, the resorbtion material may have an average resorbtion time of 1 week, 1 month, 6 months, 1 year, 2 years, 5 years, 10 years, or longer. The selection of a resorbtion time can be based on one or more factors such as, for example, the implantable device, the site of implantation, the expected lifetime of the implantable device, the expected duration of implantation, the age of the patient, expected growth rate of tissue around the implanted device, and the expected maturation rate of the capsule surrounding device. It will be recognized that there may be substantial variation from the average resorbtion time in actual devices. The actual resorbtion time may depend on the conditions within the patient's body.

Examples of suitable resorbable material include, but are not limited to, polylactide (PLA), polyglycolide (PGA), poly (lactide-co-glycolide) (PLGA), poly(e-caprolactone), polydioxanone, polyanhydride, trimethylene carbonate, poly(β-hydroxybutyrate), poly(g-ethyl glutamate), poly(DTH iminocarbonate), poly(bisphenol A iminocarbonate), poly (ortho ester)s (POEs), polycyanoacrylate, polyphosphazene, modified polysaccharides (for example, cellulose, chitin, dextran), and modified proteins (for example, fibrin, casein).

In some embodiments, the resorbable anchor arrangement may also have a drug, medication, tissue growth enhancer, or other agent disposed in the resorbable material for time release. For example, the resorbable material may be combined with a drug or other medication to treat the tissue at the implantation site or to reduce pain or inflammation. As another example, the resorbable material may be combined with a substance that promotes tissue growth and encapsulation of at least a portion of the implantable device. Generally, the drug, medication, or other agent is released over time as the resorbable material is resorbed by the patient's body.

In at least some embodiments, the anchoring arrangement is configured to enhance tissue fixation of the implantation device, to replace the anchoring arrangement, as the material is resorbed into the body of the patient. As indicated above, the anchoring arrangement may include a substance that promotes tissue growth or encapsulation. Additionally or alternatively, the shape of the anchoring arrangement may promote encapsulation; the anchoring arrangement may include grooves or pores that promote tissue in-growth to stabilize the implantable device in place; or the shape may have a three-dimensional structure that provides a scaffold to enhance and guide the direction of tissue growth. In at least some instances, the implantable device may be later removed or explanted by pulling on the device. The device preferably follows a path along the encapsulating tissue. This procedure, preferably, reduces tissue damage that would occur if the implantable device were otherwise removed.

Figure 2:
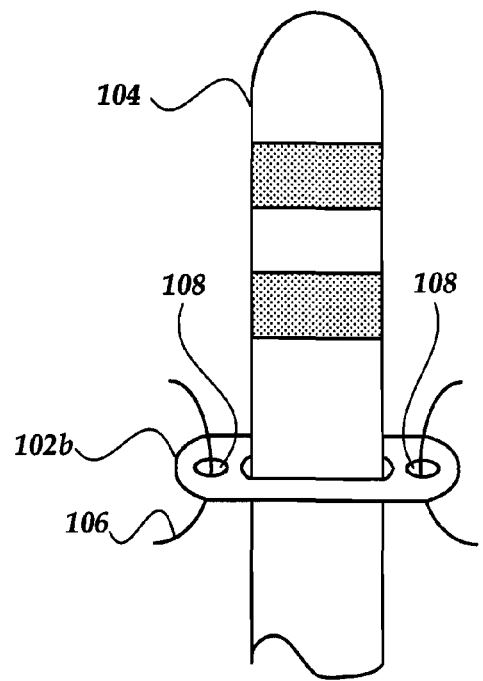
FIG. 2 is a schematic perspective view of another embodiment of an implantable device with a resorbable anchor arrangement, according to the invention.
Figure 3:
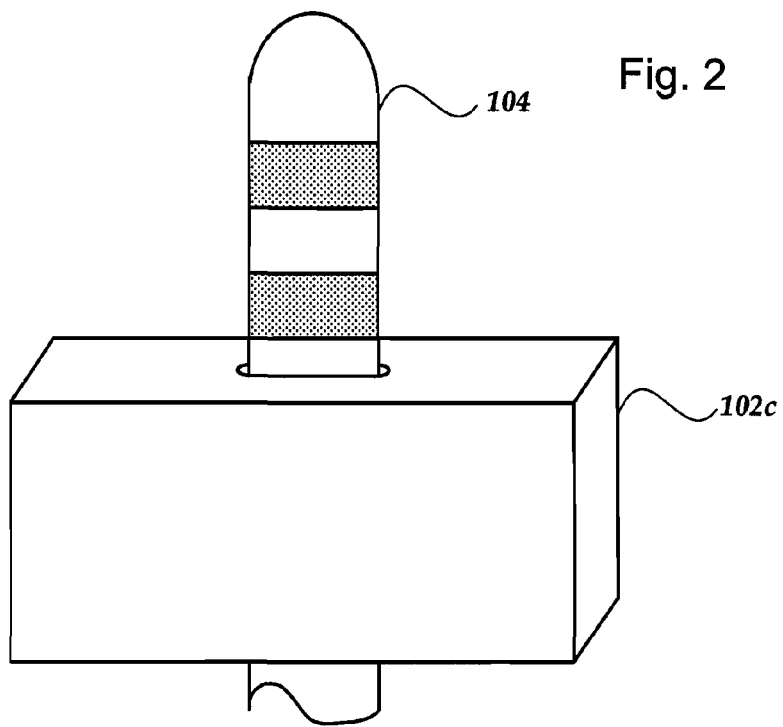
FIG. 3 is a schematic perspective view of a third embodiment of an implantable device with a resorbable anchor arrangement, according to the invention.

FIGS. 1-3 illustrate embodiments of one type of anchoring arrangement. This type of anchoring arrangement 102a, 102b, 102c fits around a portion of an implantable device, such as an electrode lead 104 (or a catheter, sensor, or transmitter.) The anchoring arrangement is at least partially, and preferably fully, formed of resorbable material. The anchoring arrangement can be formed integrally with the implantable device or the anchoring arrangement can be a separate component that can be slid onto or otherwise attached to the implantable device. In one embodiment, the anchoring arrangement is made to fit onto an existing implantable device. This can allow a practitioner or other to retrofit existing implantable devices. These anchoring arrangements 102a, 102b, 102c can be sutured, stapled, glued, or otherwise attached to the tissue of the patient to fix the implantable device in place during implantation.

The anchoring arrangement 102a of FIG. 1 fits around the electrode lead 104 so that a suture 106 or other fastener (e.g., a staple) can pass between the body of the anchoring arrangement and the lead to allow fixation of the lead to the surrounding tissue. In the illustrated example, the anchoring arrangement 102a is a ring of material, however, it will be recognized that other shapes can also be used. As the anchoring arrangement is resorbed into the body of the patient, the suture is released. The suture 106 is optionally formed of resorbable material.

The anchoring arrangement 102b of FIG. 2 includes one or more openings 108 through which a suture 106 or other fastener (e.g., a staple) can pass to allow fixation of the lead to the surrounding tissue. Although the anchoring arrangement 102b is illustrated as a separate component that can be slid onto the lead 104, it will be recognized that the anchoring arrangement can also be integrally formed with the lead. As the anchoring arrangement is resorbed into the body of the patient, the suture is released.

The anchoring arrangement 102c of FIG. 3 includes a mass of resorbable material disposed on the lead 104. In at least some instances, this anchoring arrangement can be anchored in position simply by the surrounding tissue. Optionally, the shape of the anchoring arrangement can be selected to prevent or resist rotations of the electrode lead and/or lateral or longitudinal movement of the lead when implanted in the body. In some instances, a fastener, such as a suture or staple, can penetrate the resorbable material of the anchoring arrangement 102c to provide further fixation for the lead 104. An another alternative, the anchoring arrangement 102c can be adhesively attached to surrounding tissue. Any fastener or adhesive attachment is released upon resorbtion of the material of the anchoring arrangement.

FIGS. 4-7 illustrate another embodiment of an anchoring arrangement 202. The anchoring arrangement 202 is provided as a cuff upon which one or more electrodes 206 (or sensors or catheter lumens) are disposed. The electrodes can be, for example, metal wires that are disposed on or within the material of the cuff. The electrodes 206 are (individually, collectively, or otherwise) coupled to a lead 204 that is connected to a pulse generator (not shown) which provides electrical pulses along one or more conductors 208 to the electrodes. As illustrated in FIG. 5, the cuff of the anchoring arrangement 202 can be positioned around a portion 210 of the body, such as a nerve, artery, vein, tissue, or organ. The anchoring arrangement 202 holds the electrodes 206 in place.

Preferably, the electrodes and conductors are made of a flexible electrically conducting material and can be a single strand or multiple strands. Examples of suitable materials for the electrodes and conductors include stainless steel, platinum, iridium, titanium, and the like. The electrodes and conductors can be uninsulated or insulated. Typically, those regions of the electrodes through which current is to be provided directly to the tissue are uninsulated.

The cuff of the anchoring arrangement 202 is formed, at least in part, of resorbable material which is resorbed into the body of the patient over time leaving the electrodes 206, as illustrated in FIGS. 6 and 7. As described above, tissue may be encouraged to grow around the electrodes or lead to stabilize the structure over time.

This embodiment can be modified by including one or more sensors or transmitters, in addition to or as an alternative to the electrodes. The embodiment can also be altered modified to include a catheter lumen that extends through the lead to the cuff. The cuff supports the end portion of the catheter lumen with one or more openings in the catheter lumen for providing the drug, medication, or other agent.

Another embodiment of an implantable device with an anchoring arrangement 302 is illustrated in FIGS. 8 and 9. The anchoring arrangement 302 is configured to be wrapped around a portion 310 of the body of the patient, such as a nerve, vein, artery, organ, or other tissue, as illustrated in FIG. 8. The anchoring arrangement 302 can be wrapped in any way including in a helical manner. The electrodes 306 can be carried on or in the material of the anchoring arrangement 302. The electrodes 306 are coupled to a lead 304 and conductors 308. Over time, the material of the anchoring arrangement is resorbed, as illustrated in FIG. 9, to leave the electrodes 306. This embodiment can be modified, as described above, for use with a catheter, sensor, and/or transmitter.

The electrode leads, catheters, sensors, and transmitters described herein are typically coupled to an implantable or external control unit as part of an implantable system or device. For example, an electrode lead can be coupled to an implantable pulse generator and a catheter can be coupled to an implantable or external drug delivery pump.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A stimulation system comprising:
  a device body comprising
    a lead having a distal portion and a proximal portion, the lead comprising, at least one terminal disposed on the proximal portion of the lead, and at least one conductor extending along the lead from the distal portion of the lead to the at least one terminal; and
    at least one anchoring unit disposed at the distal portion of the lead such that the at least one anchoring unit is entirely disposed distal to the lead, the at least one anchoring unit configured and arranged for anchoring the distal portion of the lead in a patient upon implantation so that the at least one anchoring unit at least partially surrounds at least one nerve of a patient, the anchoring unit being cuff-shaped and defining a slit extending along a length of the anchoring unit that is configured and arranged to enable the at least one nerve to pass through the slit as the anchoring unit is being coupled to the at least one nerve, the anchoring unit comprising at least one electrode coupled to the at least one conductor and a resorbable material that resorbs into the patient over a period of time after implantation, the resorption at least partially releasing the at least one electrode from the anchoring unit while the device body is implanted in the patient, the at least one anchoring unit is configured and arranged such that the period of time of resorption is sufficient to allow tissue ingrowth around the at least one electrode to anchor the at least one electrode prior to release of the at least one electrode due to at least a partial resorption of the anchoring unit.

2. The stimulation system of claim 1, wherein the at least one electrode is disposed on the at least one anchoring unit.

3. The stimulation system of claim 1, wherein the anchoring unit is formed integrally with the device body.

4. A method of implanting the stimulation system of claim 1, the method comprising:
  implanting the device body of the stimulation system into a patient; and
  coupling the anchoring unit of the stimulation system to at least one nerve of the patient so that the anchoring unit at least partially surrounds the at least one nerve of the patient, the anchoring unit being coupled to the device body to allow fixation of the device body to the at least one nerve.

5. The method of claim 4, further comprising enhancing tissue growth around the at least one electrode.

6. The method of claim 4, further comprising removing the device body after enough of the resorbable material is resorbed by the patient to at least partially release the at least one electrode from the anchoring unit.

7. The method of claim 4, wherein the resorption of the anchoring unit fully releases at least one of the electrodes from the anchoring unit.

8. The method of claim 4, wherein the at least one electrode is disposed on the at least one anchoring unit.

9. The stimulation system of claim 1, wherein the resorption of the anchoring unit fully releases at least one of the electrodes from the anchoring unit.

10. The stimulation system of claim 1, wherein the at least one conductor extends along at least a portion of the at least one anchoring unit in a direction that is parallel to the slit extending along the length of the at least one anchoring unit.

11. The stimulation system of claim 1, wherein the device body is configured and arranged for explantation from the patient after the resorbable material is resorbed by the patient.

12. The stimulation system of claim 1, wherein the device body further comprises an implantable pulse generator coupled to the proximal portion of the lead, wherein the implantable pulse generator provides electrical pulses along the at least one conductor to the at least one electrode.

13. The stimulation system of claim 12, wherein the implantable pulse generator is configured and arranged for implantation at a location that is remote from the at least one anchoring unit.

14. The stimulation system of claim 12, wherein the at least one terminal of the lead is configured and arranged for insertion into the implantable pulse generator.

* * * * *